(12) United States Patent
Giampapa

(10) Patent No.: US 7,414,021 B2
(45) Date of Patent: Aug. 19, 2008

(54) METHOD AND COMPOSITION FOR RESTORATION OF AGE RELATED TISSUE LOSS IN THE FACE OR SELECTED AREAS OF THE BODY

(76) Inventor: Vincent Carmine Giampapa, 12 Robinwood Dr., Little Falls, NJ (US) 07424

( * ) Notice: Subject to any disclaimer, the term of this patent is extended or adjusted under 35 U.S.C. 154(b) by 20 days.

(21) Appl. No.: 11/241,005

(22) Filed: Oct. 1, 2005

(65) Prior Publication Data
US 2006/0073178 A1  Apr. 6, 2006

Related U.S. Application Data

(60) Provisional application No. 60/615,164, filed on Oct. 1, 2004.

(51) Int. Cl.
*A61K 38/28* (2006.01)
*A61K 38/18* (2006.01)
*A61K 31/56* (2006.01)

(52) U.S. Cl. ............................ 514/2; 424/401; 514/3; 514/4; 514/54; 514/171

(58) Field of Classification Search ........................ None
See application file for complete search history.

(56) References Cited

U.S. PATENT DOCUMENTS 4,837,285 A * 6/1989 Berg et al. .................. 530/356

OTHER PUBLICATIONS

Sator et al., Skin aging and sex hormones in women—clinical perspectives for intervention by hormone replacement thereapy—2004, Experimental Dermatology, vol. 13, (supplement 4) pp. 36-40.*

* cited by examiner

*Primary Examiner*—Robert Landsman
*Assistant Examiner*—Ian Dang
(74) *Attorney, Agent, or Firm*—Melvin K Silverman; Yi Li

(57) ABSTRACT

A treatment method for restoring of age related tissue loss in the face or selected areas of the body is disclosed which includes injecting an injectable composition containing a growth factor and hyaluronic acid as a carrier into the dermis, the hypodermis, or both, in various areas of the face, or selected areas of the body of a person to stimulate collagen, elastin, or fat cell production, thereby restoring age related tissue loss in the face and selected areas of the body. Further disclosed is an injectable composition for restoring of age related tissue loss in the face and selected areas of the body, which contains a growth factor and hyaluronic acid as a carrier for providing time release of the growth factor into tissues. The growth factor can be insulin, insulin-like growth factor, thyroid hormone, fibroblast growth factor, estrogen, retinoic acid, or their combinations.

12 Claims, No Drawings

METHOD AND COMPOSITION FOR RESTORATION OF AGE RELATED TISSUE LOSS IN THE FACE OR SELECTED AREAS OF THE BODY

CROSS REFERENCE TO RELATED APPLICATION

This application claims the benefit under 35 USC 119(e) of the provisional patent application Ser. No. 60/615,164, filed on Oct. 1, 2004, which is hereby incorporated by reference in its entirety.

FIELD OF THE INVENTION

The present invention relates to methods of restoration of age related tissue loss in the face or selected areas of the body. More specifically, the method injects a combination of hyaluronic acid and a stem cell stimulating compound in one or more skin layers to stimulate collagen, elastin and fat cell productions, which restores age related tissue loss in the face or selected areas of the body.

BACKGROUND OF THE INVENTION

Skin is composed of the epidermis and the dermis. Below these layers lies the hypodermis, which is not usually classified as a layer of skin. The hypodermis is also commonly referred to as subcutaneous fat layer, or subcutaneous tissue. The outermost epidermis is made up of stratified squamous epithelium with an underlying basement membrane. It contains no blood vessels, and is nourished by diffusion from the dermis. The main type of cells which make up the epidermis are keratinocytes, with melanocytes and langerhans cells also present. This layer of skin is responsible for keeping water in the body and keeping other harmful chemicals and pathogens out.

The dermis lies below the epidermis and contains a number of structures including blood vessels, nerves, hair follicles, smooth muscle, glands and lymphatic tissue. The dermis (or corium) is typically 3-5 mm thick and is the major component of human skin. It is composed of a network of connective tissue, predominantly collagen fibrils providing support and elastic tissue providing flexibility. The main cell types are fibroblasts, adipocytes (fat storage) and macrophages. The hypodermis lies below the dermis. Its purpose is to attach the skin to underlying bone and muscle as well as supplying it with blood vessels and nerves. It is made up of loose connective tissue and elastin. The main cell types are fibroblasts, macrophages and adipocytes. The hypodermis contains 50% of body fat. Fat serves as padding and insulation for the body.

Facial aging occurs as the result of several factors: inherent changes within the skin, effects of gravity, facial muscles acting on the skin (dynamic lines), soft tissue loss or shift and bone loss and loss of tissue elasticity. The skin ages when the epidermis begins to thin, causing the junction with the dermis to flatten. Collagen decreases as a person ages and the bundles of collagen, which gives the skin turgor, become looser and lose strength. When the skin loses elasticity, it is less able to resist stretching. Coupled with gravity, muscle pull and tissue changes, the skin begin to wrinkle. Water loss and breakdown of bonds between cells also reduces the barrier function of the skin, which can cause the skin's pore size to increases.

As a person ages, the face loses volume, soft tissue, and fat. The appearance of jowls and folds are usually caused by the drooping of facial tissues and folding of areas where the muscles below are attached to the skin. As part of the reduction in soft tissue the face gets more hollow.

More specifically, in various facial areas, such as forehead, eyes, nose, midface and lower face, changes relating to aging have been well documented. In forehead area, the forehead and brow droop over time, which lowers the eyebrows and causes the upper eyelid skin to bunch. Forehead lines appear when one tries to hold the brows and eyelids up to counteract these changes. It is well known that the eyes are often the first facial feature to show signs of aging. Skin changes around the eyes occur earlier than in the rest of the face since the skin is thinner around the eyes. The skin here contains fewer glands and is subjected to constant blinking, squinting, rubbing, and pulling. The midface ages when the cheeks begin to droop, causing nasolabial folds. Nasolabial folds are the lines that run from the sides of the nose to the corners of the mouth. These folds have been treated with facial fillers. In the nose area, as a person ages, the nose elongates. Common causes of elongation are thinning of the soft tissue and loss of elasticity, which causes "drooping of the tip" and unmasking of the bone, creating a new hump. In the lower face area, as the face ages, facial tissues descend. This results in the so-called "laugh lines". Folds and lines in this area have been treated with facial fillers. Further down on the face, the corners of the mouth may droop and descent of the jowls can create folds often referred to as "marionette" lines. Furthermore, jowls form when the cheeks sag around a fixed point along the jaw where the facial muscles attach to the jawbone. The facial muscles continue down into the neck as a sheet called the platysma muscle. This muscle often gaps in the center of the neck, creating two bands.

Various injectables have been used for restoring tissue loss in the face. Since the 1980s, injectable collagen has been used as a soft-tissue filler to fill wrinkles, lines and scars on the face. Collagen is a naturally occurring protein that supports various parts of the body including skin, tendons and ligaments. Fat injections have been used for years to add volume, fill wrinkles, lines and enhance the lips. Fat injections involve taking fat from one part of the patient's body (abdomen, thighs or buttocks) and reinjecting it beneath the facial skin. Botulinum toxins have been used for neck spasms, cranial nerve disorders and eye spasms. With the recent FDA approval of Botox for cosmetic use in the glabellar region, the drug is used to smooth wrinkles. When injected into facial muscles botulinum toxins block nerve impulses, temporarily paralyzing muscles and smoothing wrinkles.

Hyaluronic acid is one of most commonly used cosmetic dermal filler which adds volume to minimize wrinkles and lines. Hyaluronic acid is a linear polysaccharide that exists naturally in all living organisms and is a universal component of the extra-cellular spaces of body tissues. The identical structure of hyaluronic acid in all species and tissues makes this polysaccharide an ideal substance for use as a bio-material in health and medicine. Hyaluronic acid is present in many places in the human body. It gives volume to the skin, shape to the eyes and elasticity to the joints. The highest concentrations are found in connective tissues, and most hyaluronic acid (about 56%) is found in the skin.

Various forms of hyaluronic acid are provided commercially by a number of manufacturers. The most commonly used hyaluronic acid is the non-animal stabilized hyaluronic acid (NASHA) in a clear gel form, produced by bacterial fermentation from streptococci bacteria. Different from animal derived hyaluronic acid, the non-animal derived hyaluronic acid is free from animal proteins. This limits the risk of animal based disease transmissions or development of allergic reactions to animal proteins. The most known non-animal stabilized hyaluronic acid is manufactured by Q-med, Seminariegatan, Uppsala, and commercially available under the tradename Restylane®. Since its commercialization in 1996, it is estimated that over 2,500,000 treatments have been carried out worldwide. Other non-animal stabilized hyaluronic acid products include Perlane® from Q-med, which has larger particles than Restylane®, and Captique™ from Genzyme Corporation. Another commonly used filler is hyaluronan manufactured by Genzyme Corporation and commercially available under the tradename Hylaform Plus. Hylaform Plus is a sterile, nonpyrogenic, viscoelastic, clear, colorless, transparent gel implant composed of cross-linked molecules of hyaluronan. Although hyaluronic acid and derivatives are the most commonly used dermal fillers, they have limited viability. The re-injection is needed every 4 to 12 months, or even shorter.

Triiodothyronine ($T^3$) and thyroxine($T^4$) are two major hormones produced by the thyroid gland in human, are essential for growth in childhood. $T^3$ and $T^4$ stimulate growth by a direct effect on tissue and by having a permissive role on growth hormone action.

It has been reported that preadipocyte stimulation with specific growth factors induces accelerated differentiation into fat cells resulting local augmentation at the injection sites. These growth factors include insulin, insulin-like growth factor, triiodothyronine ($T^3$), thyroxine ($T^4$), and retinoic acid.

On the other hand, as taught in U.S. Pat. Nos. 5,855,921 and 5,788,953 (to Somlyai) deuterium depleted water having deuterium concentration from 0.1 to 110 ppm inhibits tumor growth in animal model studies. It has also been reported in human clinical trials involving hundreds of cancer patients in Hungary that deuterium depleted water extended life span of cancer patients. It is believed that deuterium depleted water can function as an anticarcinogenic agent, since it involves in regulation of p53 protein and c-Myc protein. It is further believed that deuterium depleted water can improve the DNA repairing process.

Although various injectables have been developed and used clinically for restoration of age related tissue loss in the face over the passed 50 years, due to various limitations in the materials or compatibility with the tissues, the long term effect in restoring the tissue loss is limited. It is desirable to develop improved injectables and treatment methods to enhance the overall effects in restoration of age related tissue loss in the face or selected areas of the body, such as neck and hands.

SUMMARY OF THE INVENTION

In one aspect, the present invention is directed to a treatment method of restoring of age related tissue loss in the face or selected areas of the body of a person. In one embodiment, the treatment method comprises the steps of providing a composition comprising at least one growth factor and hyaluronic acid as a carrier; and injecting the composition into the dermis, or the hypodermis at one or more areas of the face, or selected areas of the body of a person to stimulate collagen, elastin, or fat cell production, thereby restoring age related tissue loss in the face, or the selected areas of the body of the person. The treatment method further comprises repeating the treatment session about twice, with a time interval between two sessions about one month. Upon injection the hyaluronic acid is absorbed in the dermis or the hypodermis with time, thereby providing time release of the growth factor in the composition into the dermis or the hypodermis. The growth factors can be used for the method of the present invention include insulin, an insulin-like growth factor, a thyroid hormone, a fibroblast growth factor, an estrogen, retinoic acid, or combination thereof.

In another embodiment, the treatment method comprises the steps of providing a first composition comprising a first growth factor and hyaluronic acid as a carrier; providing a second composition comprising a second growth factor and hyaluronic acid as a carrier; injecting the first composition into the dermis at one or more areas of the face, or selected areas of the body of a person to stimulate collagen and elastin productions; and injecting the second composition into the hypodermis at the at one or more areas of the face, or the selected areas of the body of the person to stimulate fat cell production; thereby restoring age related tissue loss in the face, or the selected areas of the body of the person. The treatment method further comprises repeating the treatment session about twice, with a time interval between two sessions about one month. Upon injection the hyaluronic acid is absorbed in the dermis and the hypodermis with time, thereby providing time release of the growth factor in the composition into the dermis and the hypodermis.

In a further aspect, the present invention is directed to an injectable composition for restoring age related tissue loss in the face, or selected areas of the body. The injectable composition comprises a growth factor and hyaluronic acid as a carrier for time release of the growth factor into the tissue. The growth factor can be insulin, an insulin-like growth factor, a thyroid hormone, a fibroblast growth factor, an estrogen, retinoic acid, or combination thereof.

In one embodiment, the composition comprises liothyronine sodium, levothyroxine sodium, insulin, retinoic acid and hyaluronic acid. In another embodiment, the composition comprises an estrogen and hyaluronic acid. Furthermore, the injectable composition can comprise deuterium reduced water. Optionally, the composition can further comprise dimethylaminoethanol.

DETAILED DESCRIPTION OF THE INVENTION

In one aspect, the present invention provides injectable compositions for injection into the dermis or the hypodermis (subcutaneous tissue) to restore age related tissue loss in the face, and selected areas of the body, such as neck and hands.

In one embodiment, the injectable composition comprises at least one growth factor, and hyaluronic acid as a carrier. Growth factor is a protein that acts as a signaling molecule between cells (like hormones) that attaches to specific receptors on the surface of a target cell and promote differentiation and maturation of these cells. Growth factor signifies a positive effect on cell growth and cellular differentiation. The growth factors suitable for the purpose of the present invention include, but are not limited to, insulin, insulin-like growth factor, thyroid hormone, fibroblast growth factor, estrogen, retinoic acid, or combination thereof.

Suitable thyroid hormone includes, but is not limited to, triiodothyronine ($T^3$), thyroxine ($T^4$), or combination thereof. Liothyronine is a synthetic form of the natural triiodothyronine ($T^3$) and is available as the sodium salt. The empirical formula of liothyronine sodium is $C_{15}H_{13}I_3NNaO_4$ and it has a molecular weight of 672.96. Levothyroxine sodium is a synthetic form of the natural thyroxine ($T^4$), which is identical to that produced in the human thyroid gland. Levothyroxine sodium has an empirical formula of $C_{15}H_{10}I_4NNaO_4 \cdot H_2O$, molecular weight of 798.86. In a preferred embodiment, a combination of liothyronine sodium and levothyroxine sodium is used in the injectable composition for stimulating preadipocytes to induce accelerated differentiation into fat cells.

Estrogens are a group of steroid compounds that function as the primary female sex hormone in human body. The three naturally occurring estrogens are estradiol, estriol and estrone. Suitable estrogens for the purpose of the present invention include, but are not limited to, estriol, estradiol, estrone or combination thereof. In a preferred embodiment, estriol is used for stimulating collagen or elastin production in the dermis.

As described above, hyaluronic acid is a commonly used cosmetic dermal filler, which has been used alone to add volume to minimize wrinkles and lines in the face. In the present invention, hyaluronic acid is used as a carrier in the injectable composition for time release of the growth factors into the dermis or the hypodermis. Various forms of commercially available hyaluronic acid, such as non-animal stabilized hyaluronic acid and hyaluronan, can be used for the purpose of the present invention. In an exemplary embodiment, Restylane® and Perlane®, the non-animal stabilized hyaluronic acid, manufactured by Q-med, Seminariegatan, Uppsala, can be used. In the injectable the hyaluronic acid is in a form of gel. The hyaluronic acid gel, such as Restylane® and Perlane® gel particles, is re-absorbed slowly in the injection sites. As the gel breaks down by hydrolysis, water takes its place. The less concentrated the gel becomes, the more water it is able to bind. When totally absorbed, the gel disappears unnoticed from the body. With different hyaluronic acid concentrations and gel particle sizes, the rate of absorption of the gel in the injection sites can be different, hence, the rate of releasing the growth factors in the injectable composition can be different. In this aspect, therefore, hyaluronic acid gel functions as a time release carrier, or a delivery vehicle of the growth factors in the instant injectable composition, which gradually releases the growth factors with time into the dermis or the hypodermis that receives the injection.

Furthermore, the composition can also comprise deuterium reduced water, which functions as an anticarcinogenic agent. The term "deuterium-reduced water" used herein means an aqueous fluid having a deuterium concentration substantially below a naturally occurring deuterium level in water, more specifically, having a deuterium level in a range from about 0.1 ppm to about 110 ppm. The deuterium-reduced water can be produced by distillation or electrolysis, as described in U.S. Pat. Nos. 5,855,921 and 5,788,953, which are hereby incorporated by reference in their entirety. Using electrolysis, the deuterium concentration of water can be reduced down to 30-40 ppm and further reduced to 6-20 ppm by a further electrolysis. Using distillation, the deuterium concentration of water can be reduced down to 20-30 ppm and further reduced to 1-10 ppm by further increasing the plate number and/or repeating the distillation process. To produce a large volume of water, this deuterium depleted water can be mixed with regular water in a predetermined proportion to obtain a water which has the deuterium concentration from about 80 to about 110 ppm, which is substantially lower than the natural occurring level of deuterium in water. In the injectable composition of the present invention, the deuterium reduced water can be a part of the medium, and the concentration of the deuterium reduced water can be in a range from 10 ml to 40 ml per 100 ml of the injectable composition, and preferably from 15 ml to 30 ml per 100 ml of the injectable composition. However, it should be understood that the injectable composition can also be prepared using the regular double distilled water as a medium.

Optionally, the injectable composition can also comprise dimethylaminoethanol. Dimethylaminoethanol is a precursor to acetylcholine and is used herein to enhance the muscle tone on the face or selected areas of the body. In the injectable composition of the present invention, the concentration of dimethylaminoethanol can be in a range from 2 g to 20 g per 100 ml of the injectable composition, and preferably from 5 g to 15 g per 100 ml of the injectable composition.

The injectable composition can comprise different growth factors and other components, depending on the layer of tissue to be injected. In one preferred embodiment, the injectable composition comprises an estrogen and hyaluronic acid as the carrier, as further illustrated in Example 1. This composition is preferably used for injection into the dermis to stimulate collagen and elastin productions. In one embodiment, estriol is used. The concentration of estriol can be in a range from 0.02 g to 0.2 g per 100 ml of the injectable composition, and preferably from 0.05 g to 0.15 g per 100 ml of the injectable composition. The composition can also comprise fibroblast growth factors and other suitable growth factors that stimulate collagen and elastin productions.

In another preferred embodiment, the injectable composition comprises triiodothyronine, thyroxine, insulin and hyaluronic acid, as further illustrated in Example 2. The composition further comprises retinoic acid. This composition is preferably used for injection into the hypodermis to stimulate fat cell production. Preferably, liothyronine sodium and levothyroxine sodium, the synthetic forms of triiodothyronine and thyroxine, respectively, are used. The concentration of liothyronine sodium can be in a range from 2 µg to 30 µg per 100 ml of the injectable composition, and preferably from 5 µg to 20 µg per 100 ml of the injectable composition. The concentration of levothyroxine sodium can be in a range from 10 µg to 60 µg per 100 ml of the injectable composition, and preferably from 20 µg to 40 µg per 100 ml of the injectable composition. The concentration of insulin can be in a range from 5 units to 40 units per 100 ml of the injectable composition, and preferably from 15 units to 30 units per 100 ml of the injectable composition. The concentration of hyaluronic acid can be in a range from 0.5 g to 3 g per 100 ml of the injectable composition, and preferably from 1.5 g to 2.5 g per 100 ml of the injectable composition. The concentration of retinoic acid can be in a range from 5 mg to 25 mg per 100 ml of the injectable composition, and preferably from 10 mg to 20 mg per 100 ml of the injectable composition.

Furthermore, both above described compositions can further comprise deuterium reduced water, and dimethylaminoethanol, as described above.

In a further aspect, the present invention is directed to the methods of using the compositions of the present invention for restoring age related tissue loss in the face and selected areas of the body. In one embodiment, the method comprises injecting a composition which comprises at least one growth factor and hyaluronic acid as a carrier into the dermis, or the hypodermis at one or more areas of the face and selected areas of the body of a person to stimulate collagen, elastin, or fat cell production. Preferably, three sessions of injections are administered sequentially, with a time interval of about one month.

The suitable areas, or injection sites, include, but are not limited to, the periorbital area, the lips, the malar area, the nasolabial folds, the labio-mandibular folds, and selected areas of the body, such as the neck, and the hands. The periorbital area includes the eyelids and surrounding areas including the eyebrows, bony eye socket and rims, cheeks and forehead. Malar area includes cheek or the side of the head. The nasolabial folds are the deep folds which run from the side of the nose to the corner of the mouth. The labiomandibular folds are the folds between the corner of the mouth and the jawbone.

The treatment can be performed without local or general anesthesia. Typically, a patient is placed in a treatment room, the injections are given using a 30 gauge needle with a 3 to 5 cc syringe. In about 0.1 ml increments, the dermis or the hypodermis of a specific area is treated. Example 3 shows that 40 patients were injected with the Composition B of Example 2 at various facial areas at the hypodermis level. Three sessions of injections were administered with a one month interval. The clinical follow up for up to 24 months has demonstrated a long-lasting effect of the enhancement of fat cell production in the hypodermis.

In a further embodiment, the method comprises injecting a first composition comprising a first growth factor and hyaluronic acid as a carrier into the dermis at one or more areas of the face, or selected areas of the body of a person to stimulate collagen and elastin productions; and injecting the second composition comprising a second growth factor and hyaluronic acid as a carrier into the hypodermis at the same areas of the face, or selected areas of the body to stimulate fat cell production; thereby restoring age related tissue loss in the face, neck or hands of the person. The first and the second compositions have been described above, and further illustrated in detail hereinafter in the examples.

The two layer treatment can also be performed without local or general anesthesia. In this procedure, an adjustable 30 gauge needle with a 3 to 5 cc syringe can be used to inject the first composition at selected areas at the dermis level first. With 0.1 ml increments, the dermis of a specific area is treated. Upon completing the dermal injection, the adjustable 30 gauge needle is adjusted so that the needle length is longer for injection in the subcutaneous tissue (hypodermis). Alternatively, the needle can be changed to a longer one for subcutaneous injection. The second composition is then injected in the same selected areas, at the hypodermis level. Preferably, three sessions of injections are administered sequentially, with a time interval of about one month.

Example 4 shows about 200 patients have been treated in the past two years using the two layer treatment. The ongoing improvement in skin quality has been observed and documented by professional photographs. The improvement has been noted to be markedly better than injection of hyaluronic acid alone. It has been found that using the compositions and the method of the present invention has resulted in an ongoing increase in both volume and skin turgor, and improvement of texture and tightness. This is substantially different from the temporary filling that can be achieved by injection of hyaluronic acid alone.

Furthermore, it has been found that upon completion of the three sessions, most patients achieve a long term improvement on their facial appearance. Different from the traditional hyaluronic acid injection which needs to be repeated every four to six months, using the treatment method of the present invention described above, upon completion of the three sessions, no repetitive injections are needed. However, if a person desires a further improvement in the selected areas, additional treatment as described above can be provided.

Without being bound to any theory, it is believed that in the two layer injection method of the present invention, the introduction of suitable growth factors, with hyaluronic acid as the delivery vehicle, into the hypodermis level stimulates preadipocytes (the precursors of fat cells) and induces their accelerated differentiation into mature adipocytes (fat cells) at the injection sites; while introduction of specific growth factors, such as estrogen, into the dermis stimulates elastin and collagen productions. The combination of the effects achieved in the dermis layer and the underlying hypodermis layer results in the restoration of age related tissue loss at the treatment sites.

It should be understood that although the method of the present invention has been illustrated with the restoration of age related tissue loss in the face, the method can be used in other selected areas of the body, such as the neck, and hands, for the same purpose.

The following examples are illustrative of the invention and are in no way to be interpreted as limiting the scope of the invention, as defined in the claims. It will be understood that various other ingredients and proportions may be employed, in accordance with the proceeding disclosure.

EXAMPLE 1

The following Composition A was prepared for injection into the dermis.

| Composition A | |
|---|---|
| Component | Concentration (amount/100 ml) |
| Estriol | 0.091 g |
| Hyaluronic acid | 1.91 g |
| Deuterium reduced water | 22.73 ml |

The Composition A was prepared by mixing 3.18 ml of a hyaluronic acid injectable containing 60 mg/ml of hyaluronic acid with 4.55 ml of an estriol injectable containing 2 mg/ml estriol and 2.27 ml of deuterium reduced water. The formed Composition A was dispensed into multiple sterile syringes for use. All materials used are sterilized using known sterilization equipments and techniques, such as autoclave, convection oven, or filtering with 0.2 µm filter. It is noted that the deuterium reduced water can be purchased commercially, or produced by distillation or electrolysis using the methods described in U.S. Pat. Nos. 5,855,921 and 5,788,953.

EXAMPLE 2

The following Composition B was prepared for injection into the subcutaneous tissue.

| Composition B | |
|---|---|
| Component | Concentration (amount/100 ml) |
| Liothyronine sodium | 9.09 µg |
| Levothyronine sodium | 34.09 µg |
| Humulin R | 18.18 unit |
| Hyaluronic acid | 1.91 g |
| Deuterium reduced water | 22.73 ml |

The Composition B was prepared by mixing 3.18 ml of a hyaluronic acid injectable containing 60 mg/ml of hyaluronic acid with 4.55 ml of a liothyronine/levothyroxine mixture injectable containing 0.2 µg of liothyronine sodium and 0.75 µg of levothyroxine sodium, 18.18 unit of Humulin R injectable and 2.27 ml of deuterium reduced water. The formed Composition B was dispensed into multiple sterile syringes for use. All materials used are sterilized using known sterilization equipments and techniques, such as autoclave, convection oven, or filtering with 0.2 μm filter. It is noted that liothyronine sodium and levothyroxine sodium can be obtained from Professional Compounding Centers of America, Houston, Tex. Humulin R injectable is an insulin human regular injectable manufactured by Eli Lilly and Company, Indianapolis, Ind.

EXAMPLE 3

40 patients were injected with the Composition B of Example 2 at various facial areas at the hypodermis level. The injection sites included the peri-orbital area, the lips, the malar area, the nasolabial folds and the labio-mandibular folds. Epinephrine-soaked sponges were used on all patients to avoid post-procedure swelling and bruising. Three sessions of injections were administered one month apart from one another. All patients tolerated the procedure well and no complications were reported.

The patients were followed after 3, 6, 9, 18 and 24 months, respectively. Professional photographs were used as the documents. It was found that the enhancement of fat cell production in the hypodermis had a long-lasting effect, which is substantially different from the temporary filling effect that can be achieved by injection of hyaluronic acid alone.

EXAMPLE 4

About 200 patients were treated with the two layer treatment method. A patient was placed in the treatment room and the injection was given without any form of local or general anesthesia. An adjustable 30 gauge needle with a 3 to 5 cc syringe was used to inject the Composition A of Example 1 at selected areas at the dermis level first. With 0.1 ml increments, the dermis of a specific area was treated. Upon completing the dermal injection, the adjustable 30 gauge needle was adjusted so that the needle length was longer for injection in the subcutaneous tissue. Alternatively, the needle could be changed to a longer one for subcutaneous injection. Then, the Composition B of Example 2 was injected in the same selected areas, at the hypodermis level. The injection sites included the peri-orbital area, the lips, the malar area, the nasolabial folds and the labio-mandibular folds. Epinephrine-soaked sponges were used on all patients to avoid post-procedure swelling and bruising. All patients tolerated the procedure well and no complications were reported.

The patients were followed after 3, 6, 9, 18 and 24 months, respectively. Professional photographs were used as the documents. It was observed that the treatment resulted in not only a temporary filling, but an ongoing increase in both volume and skin turgor, texture and tightness. The restoration of age related tissue loss is markedly better than the existing method of using hyaluronic acid alone as a filler.

While the present invention has been described in detail above, these should not be construed as limitations on the scope of the present invention, but rather as an exemplification of preferred embodiments thereof. It will be apparent, however, that various modifications and changes can be made within the spirit and the scope of this invention as described in the above specification and defined in the appended claims and their legal equivalents.

What is claimed is:

1. A treatment method for restoring of tissue volume, skin turgor, texture and tightness in the face or selected areas of the body of a person comprising the steps of:
   (a) providing a composition comprising liothyronine sodium, levothyroxine sodium, insulin, and hyaluronic acid as a carrier; and
   (b) injecting said composition into the dermis, or the hypodermis at one or more areas of the face, or selected areas of the body of a person, thereby restoring tissue volume, skin turgor, texture and tightness in the face, or said selected areas of the body of said person.

2. The treatment method of claim 1 further comprising repeating the step (b) for about two times, with a time interval about one month.

3. The treatment method of claim 1, wherein upon injection said hyaluronic acid is absorbed in the dermis or the hypodermis with time, thereby providing time release of said composition into the dermis or the hypodermis.

4. The treatment method of claim 1, wherein said one or more areas is the peri-orbital area, the lips, the malar area, the nasolabial folds, the labio-mandibular folds, the neck, or the hands.

5. The treatment method of claim 1, wherein said composition further comprises retinoic acid.

6. The treatment method of claim 1, wherein said composition further comprises deuterium reduced water.

7. A treatment method for restoring of tissue volume, skin turgor, texture and tightness in the face or selected areas of the body of a person comprising:
   (a) providing a composition comprising an estrogen and hyaluronic acid; and
   (b) injecting said composition into the dermis, or the hypodermis at one or more areas of the face, or selected areas of the body of a person, thereby restoring tissue volume, skin turgor, texture and tightness in the face, or said selected areas of the body of said person.

8. A treatment method for restoring tissue volume, skin turgor, texture and tightness in the face, or selected areas of the body of a person comprising the steps of:
   (a) providing a first composition comprising an estrogen and hyaluronic acid as a carrier;
   (b) providing a second composition comprising liothyronine sodium, levothyroxine sodium, insulin, and hyaluronic acid as a carrier;
   (c) injecting said first composition into the dermis at one or more areas of the face, or selected areas of the body of a person; and
   (d) injecting said second composition into the hypodermis at said one or more areas of the face, or said selected areas of the body of said person;
   thereby restoring tissue volume, skin turgor, texture and tightness in the face, or said selected areas of the body of said person.

9. The treatment method of claim 8 further comprising repeating the steps (c) and (d) for about two times, with a time interval about one month.

10. The treatment method of claim 8, wherein upon injection said hyaluronic acid is absorbed in the dermis and the hypodermis with time, thereby providing time release of said first composition and said second composition into the dermis and the hypodermis, respectively.

11. The treatment method of claim 8, wherein said one or more areas is the peri-orbital area, the lips, the malar area, the nasolabial folds, the labio-mandibular folds, the neck, or the hands.

12. The treatment method of claim 8, wherein said second composition further comprises retinoic acid.

* * * * *